(12) United States Patent
Kumar

(10) Patent No.: US 6,821,531 B2
(45) Date of Patent: Nov. 23, 2004

(54) POWDERED/MICROFIBRILLATED CELLULOSE

(75) Inventor: Vijay Kumar, Coralville, IA (US)

(73) Assignee: Iowa Research Foundation University of Iowa, Iowa City, IA (US)

( * ) Notice: Subject to any disclaimer, the term of this patent is extended or adjusted under 35 U.S.C. 154(b) by 109 days.

(21) Appl. No.: 09/946,658

(22) Filed: Sep. 5, 2001

(65) Prior Publication Data

US 2002/0061335 A1 May 23, 2002

Related U.S. Application Data

(60) Provisional application No. 60/232,657, filed on Sep. 14, 2000.

(51) Int. Cl.⁷ .................................................. C08B 1/00
(52) U.S. Cl. ........................ 424/488; 424/499; 424/464; 536/56; 536/57
(58) Field of Search ................................ 424/488, 499, 424/464, 408; 536/56, 57

(56) References Cited

U.S. PATENT DOCUMENTS

| | | |
|---|---|---|
| 4,159,345 A | 6/1979 | Takeo et al. |
| 4,438,263 A | 3/1984 | Morse |
| 5,830,576 A * | 11/1998 | Mehra et al. ............... 424/408 |

FOREIGN PATENT DOCUMENTS

| | | |
|---|---|---|
| JP | 59004601 | 11/1984 |

OTHER PUBLICATIONS

Whitmore et al. "Factors influencing the regeneration of cellulose I fro mphosphoric acie", Jun. 1985, Int. J. Biol. Macromol., Vo 7, pp. 182–186.*

Araki, T., et al. Chemical Abstracts, "Preparation of Microcrystalline Cellulose by Aging Alkali Cellulose," vol. 78, No. 4, Jan. 29, 1973.

* cited by examiner

Primary Examiner—Sreeni Padmanabhan
Assistant Examiner—Gina C. Yu

(57) ABSTRACT

A new cellulose excipient suitable for use as a binder, filler, and/or disintegrant in the development of solid dosage forms and as a bodying agent or a drug carrier in the preparation of topical formulations is described. The cellulose excipient is formed by soaking a source of cellulose in an aqueous alkali metal hydroxide solution. The cellulose is then regenerated, washed, and optionally hydrolyzed with a dilute mineral acid. The cellulose excipient is also useful as an aqueous dispersion in topical formulations and in the manufacture of cellulose beads.

8 Claims, 3 Drawing Sheets

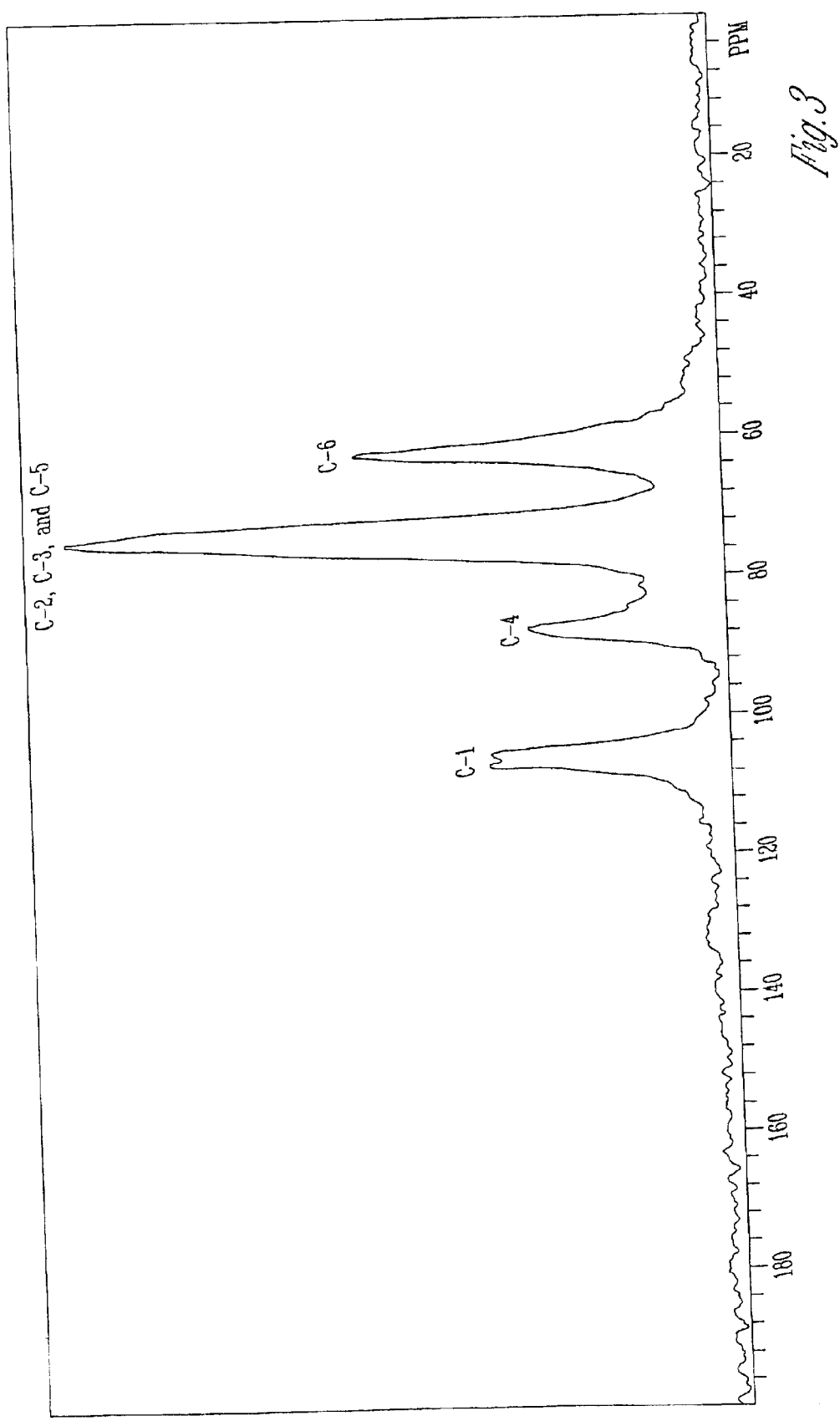

POWDERED/MICROFIBRILLATED CELLULOSE

This application claims priority to U.S. Provisional Application Ser. No. 60/232,657 filed Sep. 14, 2000.

FIELD OF THE INVENTION

This invention relates to the manufacture of a new cellulose excipient suitable for use as a filler, binder, and/or disintegrant in solid dosage forms and as a bodying agent or drug carrier in the development of topical formulations.

BACKGROUND OF THE INVENTION

Solid compacts/tablets containing an active ingredient are prepared by either wet granulation or direct compression of a mixture of powders of various components. The number and types of components in a mixture depends on the desired properties of the drug, i.e., whether it is intended for immediate release or delayed and/or controlled release. Typically, the components include a drug, a filler (or diluent), a binder, a lubricant, and/or a glidant. A disintegrant is added if the tablet is intended for immediate release of the drug. The disintegrant promotes disintegration of the tablet into a fine powder by facilitation the penetration of water into the tablet mass. The filler is added to increase the bulk of the tablet to facilitate handling and manufacture. The use of a binder in the mixture increases the cohesiveness of powder and hence facilitates the formation of the tablet. Lubricants reduce the friction between the tablet and the die wall and therefore prevent sticking of the powder bed or tablets to the punches. Glidants, in contrast, are added to improve the flow characteristics of the materials. It is imperative that tabletting excipients be inexpensive, physiologically inert, physically and chemically stable, and compatible with the other tablet components.

The preparation of tablets by direct compression has steadily increased due to the ease of manufacture. Currently, in the United States, about 50% of tablets are made by the direct compression method. Of the various materials known, microcrystalline cellulose and powdered cellulose are perhaps the most commonly and widely used direct compression excipients. Microcrystalline celluloses are prepared by chemical disintegration of cellulose. Battista, O. A. (1950), Hydrolysis and Crystallization of Cellulose, Industrial and Engineering Chemistry 42:502–507; Battista U.S. Pat. No. 2,978,446.

In general, the process of preparing microcrystalline cellulose involves hydrolyzing the cellulose with an aqueous dilute solution of a strong mineral acid, with occasional or constant stirring, at an appropriate temperature for a period until the level off degree of polymerization (level-off DP) cellulose composed of crystalline aggregates is achieved. Powdered celluloses, in contrast, are produced by mechanical disintegration of cellulose, wherein the cellulose source is first compacted into a dense sheet, then either milled to produce fine particles or converted into granules and then fractionated by passage through one or more sieves to produce the desired cellulose granules (see e.g. Morse, U.S. Pat. No. 4,269,859) or alternatively, a finally divided form of cellulose is dispersed in water and then treated with an agglutinating agent. Filtration, followed by washing the agglutinated solid first with water and then with a water-miscible organic solvent, and subsequently, lyophilizing and freeze-drying yields the product (see e.g. Morse, U.S. Pat. No. 4,438,263 (1984)).

Currently, both microcrystalline cellulose and powdered cellulose are commercially available under various trade names in different grades and types. Of these, the most common and widely used microcrystalline and powdered cellulose products are sold under the tradenames Avicel™ PH (FMC Corporation, Philadelphia, Pa.) and Solka Floc™ (Penwest Company, Patterson N.Y.).

Recently, a new direct compression excipient called low crystallinity cellulose, having a degree of crystallinity value between 15 and 45% has been developed. See e.g. Banker and Wei, U.S. Pat. No. 5,417,984. It is produced by reacting cellulose with phosphoric acid first at room temperature for about an hour and then at 45–75° C. for about 2–10.5 hours, followed by precipitation in water. Compared to microcrystalline cellulose (Avicel® PH-101), this material has been shown to possess superior properties as a binder.

The use of alkali metal hydroxides as swelling agents for cellulose has been extensively investigated. See e.g. Krassig, H. A. (1996), Cellulose Structure, Accessibility, and Reactivity, Gordon and Breach Science Publishers, Polymer Monographs, Volume 11. B. F. Wood, A. H. Conner, and C. G. Hill, Jr., A. Appl. Polym., 37:1371 (1989); C. Lin et al., ibid., 42, 417 (1991) and 45:1811 (1992). The emphasis of this research, however, has been (i) to convert cellulose into alkali cellulose for subsequent reactions to produce cellulose ethers, esters, xanthates, etc.; (ii) to improve the physical and chemical characteristics of cellulose, especially its reactivity with other agents; (iii) to study the hydrolysis kinetics of mercerized celluloses, (iv) for mercerizing treatments in textiles finishing to increase dye affinity, improve luster and smoothness, and achieve dimensional stability and raise tensile strength of fibers in the fabric, and (v) in the processing of cellulose hydrates fibers and films.

The present inventor has now discovered that soaking cellulose powder in an aqueous solution of alkali metal hydroxide and then precipitating it with ethanol and subsequently washing with water, or alternatively soaking cellulose pulp or sheet in an aqueous solution of alkali metal hydroxide, followed by washing with water and subsequently hydrolyzing with a dilute hydrochloric acid, produces a material that can be compressed into a tablet, with or without the aid of a binder, or used, optionally with other agents, in the development of a capsule dosage form. Further, the solid dosage form prepared in accordance with this invention rapidly disintegrates in water. The new cellulose excipient is also suitable as a drug carrier and/or bodying agent in the development of semisolid formulations with potential applications in pharmaceutical, food, cosmetic, and agricultural products.

Accordingly, it is a primary objective of the present invention to provide a cellulose excipient that can be used as a binder, a filler, and/or a disintegrant in the design of solid dosage forms.

It is a further objective of the present invention to provide a cellulose excipient that is directly compressible without the inclusion of a separate binder.

It is still a further objective of the present invention to provide a cellulose excipient that provides fast disintegrating properties.

Yet a further objective of the present invention is to provide a cellulose excipient that is economical to manufacture.

The method and means of accomplishing each of the above objectives as well as others will become apparent from the detailed description of the invention which follows hereafter.

SUMMARY OF THE INVENTION

The present invention describes a rapid and economical method of producing a cellulose excipient that can be compressed into a tablet without the aid of a binder. Compressed tablets made in accordance with this invention readily swell and disintegrate in water.

The cellulose excipient is prepared by (a) soaking a powdered source of cellulose in an alkali metal hydroxide, followed by precipitation with an alcohol, or (b) soaking a cellulose fiber or sheet source in an alkali metal hydroxide, then washing the swollen cellulose with water and subsequently reacting with a dilute mineral acid, first at room temperature and then at boiling temperature for a period of time sufficient to form a powder. The powdered product is then filtered and washed. The wet cake of the new excipient can be resuspended in water, or hydroalcoholic solutions, and mixed with adequate amounts of a suspending agent to produce a variety of stable dispersions. Such dispersions of the cellulose excipient can also be readily converted to cellulose beads or formulated into topical pharmaceutical and/or cosmetic compositions to treat a variety of skin disorders.

BRIEF DESCRIPTION OF THE DRAWINGS

FIG. 3 shows the solid-state carbon-13 cross-polarization magic angle spinning nuclear magnetic resonance spectrum of the cellulose excipient of this invention and that of a commercial microcrystalline excipient.

DETAILED DESCRIPTION OF THE PREFERRED EMBODIMENT

Figure 1:
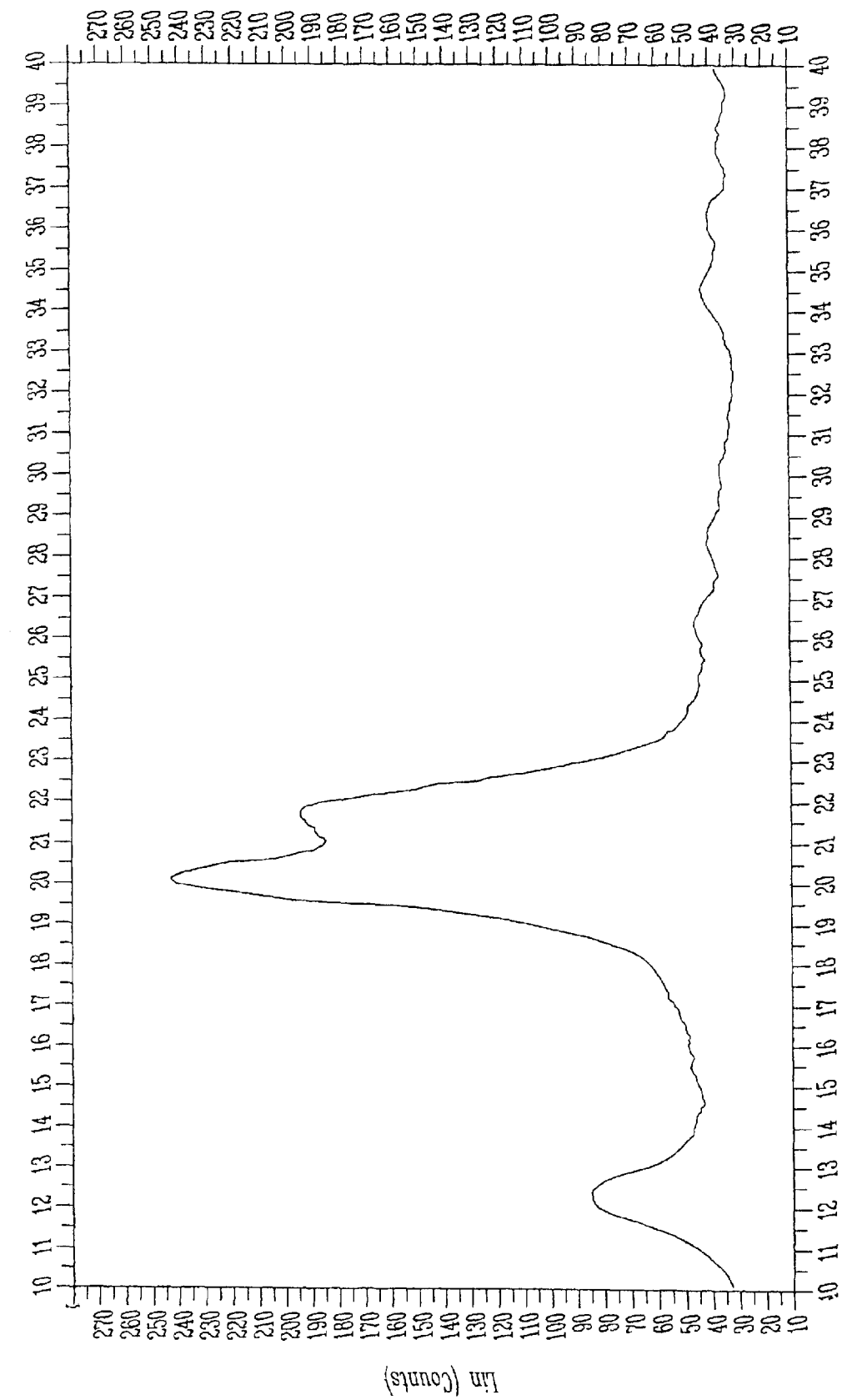
FIG. 1 shows the powder X-ray diffraction pattern of the cellulose excipient of this invention.

The present invention relates to the development of a novel powdered/microfibrillated cellulose excipient suitable for use as a filler-binder-disintegrant in the design and development of solid compacts and capsules, as a drug carrier or bodying agent in the manufacture of dermatological products, and in the form of cellulose beads for use in controlled release products or as immobilizing agents. The procedure involves soaking cellulose in an aqueous alkali metal hydroxide solution, followed by precipitation of the cellulose with an alcohol or, in the case of cellulose pulp or sheet, with water and subsequent hydrolysis with a dilute mineral acid, preferably with hydrochloric acid.

The preferred starting cellulose material for use in this invention is hydrolyzed or mechanically disintegrated cellulose powders prepared from cotton linter, alpha-cellulose, hard or soft wood pulp, purified wood pulp, cotton linter sheet, or the like. Other sources of cellulose include commercially available cellulose excipients, such as microfibrillated cellulose, powdered cellulose, regenerated cellulose, microcrystalline cellulose, and low crystallinity celluloses.

The starting cellulose material is then soaked in an aqueous alkali metal hydroxide solution for between about 0.5–72 hours at room temperature. The preferred soaking time is about 4–48 hours, depending on the batch size of the treatment, strength of the alkali metal hydroxide, and the nature of the cellulose source used. Appropriate alkali metal hydroxides for this purpose include sodium hydroxide and potassium hydroxide in concentrations of 5N or greater. The preferred alkali metal hydroxide is sodium hydroxide in a concentration of 5 N or greater, with about 5 to 7.5N being preferred for powdered celluloses and about 7.5 to 12.5 N for cellulose pulp or cellulose sheet.

It is important that the aqueous alkali metal hydroxide solution be used in sufficient quantities to completely soak and convert the starting cellulose to a pasty-looking or swollen mass. In this regard, a 1:6 weight to volume ratio of cellulose to alkali metal hydroxide is preferred. However, other ratios of cellulose to alkali metal hydroxide are also suitable for this purpose. The ratio of cellulose to alkali metal hydroxide may also depend on the types of starting cellulose material and/or alkali metal hydroxide solution used. Constant agitation of the alkali metal hydroxide solution during mixing of the cellulose powder can be used to facilitate rapid dispersion and preparation of a homogeneous gel.

The next step in the process is precipitation of the cellulose from the gel or swollen cellulose mass. In the case of gel, an alcohol in an amount to bring the total concentration of alcohol in the mixture to a range of between about 20–75% by weight, with about 25–60% by weight being preferred, is added. Appropriate alcohols for this purpose include ethanol, methanol, isopropyl alcohol, propylene glycol, etc. The preferred alcohol is ethanol. Other water-miscible organic solvents can also be used. The cellulose powder is then filtered and washed with water to a neutral pH.

It should be noted that the washing of the precipitated cellulose powder with an acid followed by acetone or an alcohol results in a material that forms tablets that do not disintegrate as rapidly as the tablets prepared using the process of this invention. Likewise, precipitation of the cellulose gel with water instead of alcohol and subsequent washing with water or ethanol produces a product that forms tablets that do not disintegrate as rapidly as tablets formed by precipitation of the gel with alcohol and subsequent washing with water or alcohol. Further, precipitation of the cellulose gel with water produces a colloid/suspension, which is difficult to filter and process.

With swollen cellulose fibers (pulp or small pieces of cotton linter sheet), obtained after soaking with an alkali metal hydroxide solution, the alcohol treatment step is optional. The material can be directly washed with water until the filtrate shows a near neutral pH. The wet swollen cellulose fibers are then treated with a dilute mineral acid at boiling temperature for 1–1.5 hours or for a period until a fine powder is formed. Suitable mineral acids for this purpose include sulfuric acid, hydrochloric acid, nitric acid, etc. in a concentration of between about 0.5–2.5N, with about 1N hydrochloric acid (HCl) being preferred. The fine powder is then filtered, and washed with water to a neutral pH. The dried powder, compared to that produced using a powdered cellulose source followed by treatment with an alkali metal hydroxide (method a), produces tablets that disintegrate relatively slowly, and hence is preferred for preparing a slowly disintegrating tablet.

The cellulose excipient obtained through the process of this invention can be used in the form of a wet mass to produce pharmaceutical colloids, suspensions, etc. Alternatively, the cellulose excipient may be dried using conventional drying procedures, such as air-drying, spray-drying, belt drying, freeze-drying, drum drying, or flash drying. A preferred drying method is in an oven at 40–55° C. for a period until the product shows a moisture content value of $\leq 8\%$, on a weight basis.

The particle size distribution and degree of polymerization (DP) of the new excipient depend on the particle size and DP of the starting cellulose powder, the strength of the acid and the duration and temperature of the acid treatment step (when swollen cellulose pulp or sheet pieces are the cellulose source), and the drying conditions employed. The true density of the new excipient varies between 1.40–1.60 g/cm$^3$, whereas the bulk and tap densities of the new material typically range between 0.2–0.5 g/cm$^3$ and 0.4–0.7 g/cm$^3$, respectively. The method produces nearly quantitative yields of the new cellulose excipient, based on the weight of the starting cellulose source being used.

The new cellulose excipient is a partially aggregated fibrous material. The powder X-ray diffraction (XRD) pattern of the new material is shown in FIG. 1. The presence of reflections at about 12, 20, and 22° 2θ indicates the cellulose excipient of this invention contains the cellulose II lattice, similar to that identified in mercerized celluloses prepared from ramie and cotton fibers and regenerated celluloses prepared from concentrated (85% w/v) phosphoric acid solutions. It must be noted that the ratio of peak intensity at 20° 2θ and 22° 2θ varies for the new product prepared using cotton linters (in the form of sheets) as the starting cellulose source, depending on the strength of sodium hydroxide and/or soaking duration of cotton linters in sodium hydroxide. In general, the intensity of peak at 22° 2θ increases with increasing the strength of sodium hydroxide or increasing the soaking duration at a given strength of sodium hydroxide used. The XRD patterns of microcrystalline celluloses and powdered celluloses reported in the literature, in contrast, show peaks at about 14, 16, 20, and 22.5° 2θ due to the presence of the cellulose I lattice. In certain cellulose materials (e.g., Avicel™ PH-301 and hydrocellulose), a peak appearing as a shoulder at about 20° 2θ has also been noted. Kumar and Kothari, Int. J. Pharm., 177:173 (1999).

The degree of crystallinity of the new cellulose excipients varies between 35% and 100%, expressed with respect to a crystalline cellulose I reference, depending on the processing conditions used, including concentration of the alkali metal hydroxide, soaking duration in the alkali metal hydroxide solution, nature of the cellulose source, the strength of the acid and the duration of acid treatment employed.

The degree of polymerization (DP) of the new product was determined according to the procedure described in the U.S. Pharmacopeia/National Formulary (USP 24/NF 19), page 2432. The value ranged between 20 and 760, depending on the DP of the starting cellulose powder employed (Method A) or on the duration of acid treatment with sodium hydroxide (Method B). The new product with a DP value between 74–350 is preferred.

The new materials showed a residue on ignition value of 0.044% and passed the test for heavy metals, as determined according to the procedure described in USP 24/NF 19, page 2432+USP<281> page 1862 (specification <0.05%) and USP <231> page 1859, Method II, specification <0.001%, respectively.

Figure 2:
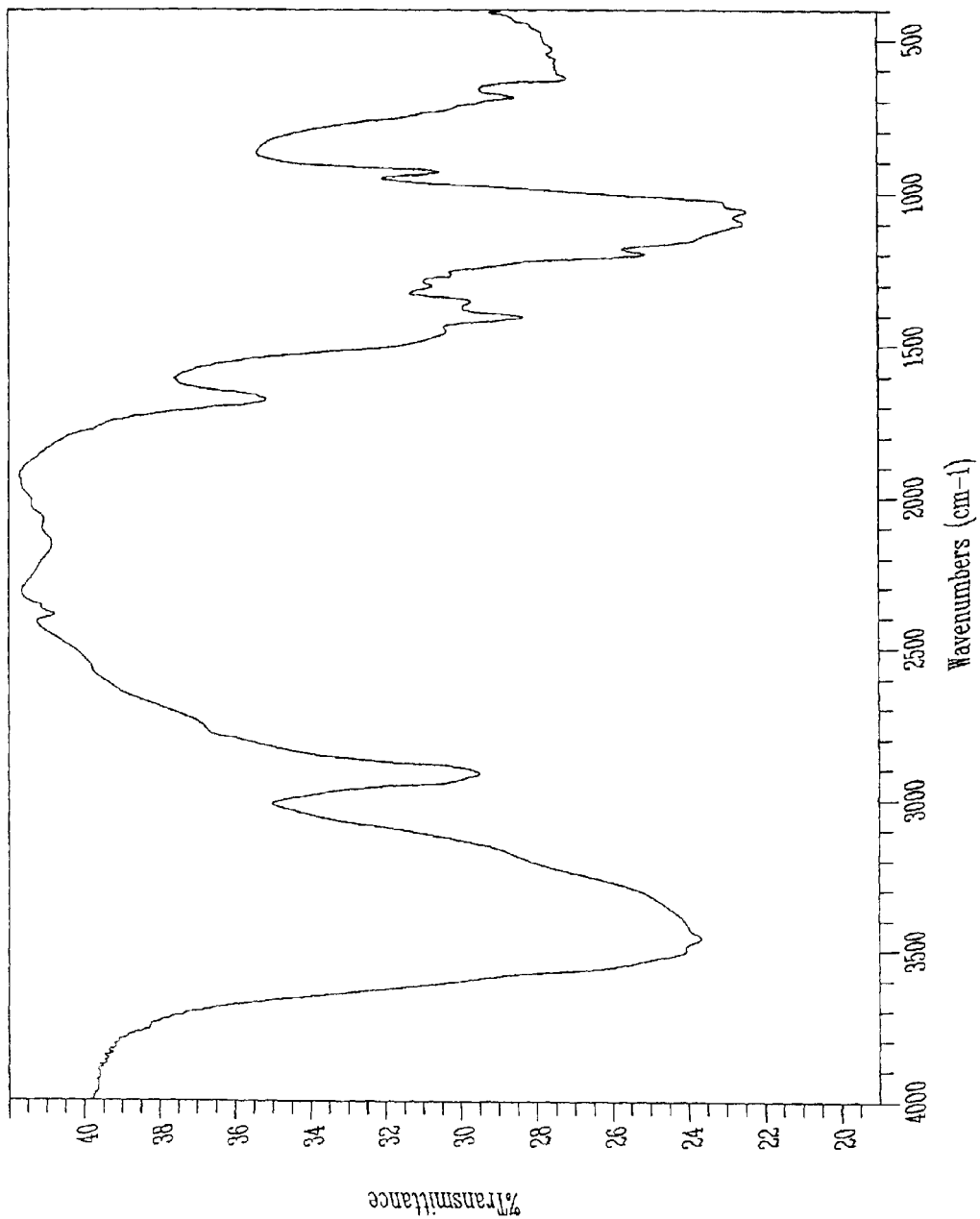
FIG. 2 shows the Fourier-transform infrared spectrum of the cellulose excipient of this invention.

The infrared spectrum of the new cellulose excipient of this invention is shown in FIG. 2. It shows essentially the same peaks pattern as that of publicly available cellulose excipient sold under the tradename Avicel™ PH grades (microcrystalline cellulose) except for the differences in the shape of the peak at 3419 cm$^{-1}$ and in the intensity of peaks at 1431 cm$^{-1}$, 1325 cm$^{-1}$, and 1115 cm$^{-1}$. This difference may be due to the different crystal lattice of the new excipient compared to that of Avicel™. There are no new peak(s) in the spectrum of the new excipient, suggesting that the new excipient is chemically similar to microcrystalline cellulose.

The carbon-13 cross-polarization nuclear magnetic resonance ($^{13}$C CP/MAS) spectrum of the new excipient is shown in FIG. 3. The signals at 106.4, 87.5 and 62.5 ppm are due to C-1, C-4, and C-6 carbons, whereas the carbon resonance at 74.6 is attributed to C-2, C-3, and C-5.

The new cellulose excipient of this invention is readily convertible into powder, bead, and hydrated forms for a variety of different purposes. For instance, the cellulose excipient of this invention can function as a binder-filler-disintegrant, all in one. This is a distinct advantage over conventional cellulose excipients, which historically have only served as binder-fillers. This novel cellulose excipient therefore simplifies the manufacturing procedure by allowing for the manufacture of pharmaceutical dosage forms without the addition of a separate disintegrant, which in turn decreases manufacturing costs.

The resulting tablet containing the binder-filler-disintegrant of this invention disintegrates rapidly in water to produce the fine particles used to prepare tablets. These superior disintegrating properties are attributed to the higher affinity of the new cellulose excipient to water molecules. The cellulose excipient is typically included in the compact in a concentration of from about 0.5–99% by weight, depending on the properties of the end product desired.

The cellulose excipient can be readily converted into an aqueous dispersion by mechanical attrition in water, with or without the aid of a suspending or viscosity enhancing agent such as carboxyalkylcellulose (e.g., sodium carboxymethylcellulose), hydroxyalkylcellulose (e.g., hydroxyethyl- and hydroxypropylcellulose), hydroxyalkylalkylcellulose (e.g., hydroxypropylmethylcellulose), polyacrylic acid (e.g., Carbopol/triethanolamine or an alkali metal hydroxide solution), polyvinylpyrrolidone (e.g., Plasdone™), etc., or a surface acting, wetting, or emulsifying agent, such as Poloxamers, polysorbates, sodium lauryl sulfate, etc. These cellulose dispersions, in turn, can be used in the manufacture of dermatological and cosmetic formulations, such as creams, lotions, ointments, emulsions, and gels.

The formulation of pharmaceutically-acceptable dermatological and cosmetic preparations is well known in the art. Generally, cosmetic and dermatological preparations may comprise auxiliaries such as preservatives, bactericides, perfumes, substances for preventing foaming, dyes, pigments which have a coloring action, thickeners, surface-active substances, emulsifiers, softening, humidifying and/or humectant substances, fats, oils, and waxes. Other customary constituents of cosmetic and/or dermatological formulations include alcohols, polyols, polymers, foam stabilizers, electrolytes, organic solvents, and silicone derivatives.

If the formulation is a lotion, appropriate solvents that may be used are: 1) water or aqueous solutions; 2) oil, such as triclycerides of capric or caprylic acid; 3) fats, waxes and other naturally occuring and synthetic fat substances, preferably esters of fatty acids with alcohols of low C number, for example isopropanol, propylene glycol or glycerol, or esters of fatty alcohols with alkanoic acids of low C number or with fatty acids; 4) alcohols, diols, or polyols of low C number, and ethers thereof, preferably ethanol, isopropanol, propylene glycol, glycerol, ethylene glycol, ethylene glycol monoethyl, monoethyl or monobutyl ether, propylene glycol monomethyl, monoethyl or monobutyl ether, diethylene glycol monomethyl or monoethyl ether and analogous products. Mixtures of these solvents may also be used. Water can be a further constituent of alcoholic solvents.

Emulsions according to the invention may include, for example, the fats, oils, waxes, and other fatty substances set forth above, as well as water.

Ointments are generally water in oil preparations which may include hydrocarbon bases, such as petrolatum, and other oleaginous bases such as lard, benzoinated lard, olive oil, cottonseed oil, gelled mineral oil, and other oils.

Gels according to the invention usually comprise alcohols of low C number, for example ethanol, isopropanol, 1,2-propanediol, glycerol and water, or the above-mentioned oils in the presence of a thickener, which may be silicon dioxide or an aluminum silicate in oily-alcoholic gels and is preferably a polyacrylate in aqueous-alcoholic or alcoholic gels.

Solid sticks according to the invention may comprise, for example, naturally occuring or synthetic waxes, fatty alcohols or fatty acid esters.

Dermatological and cosmetic formulations which include the cellulose excipient of this invention may further include a variety of substances, including suitable stabilizers, wetting, and dissolving agents as well as colorings, moisturizers, preservatives, and fragrances. These minors are added in small amounts and are conventionally known in pharmaceutical formulation work to enhance elegance. Such minors should comprise less than 1% of the overall composition. Dermatological and cosmetic formulations of this invention will generally include from about 0.5–25% by weight of the cellulose excipient, with about 2–10% by weight being preferred.

In addition, the aqueous dispersions described above can be spray dried to produce cellulose beads or particles, which may be used as tabletting aids for controlled release formulations, as immobilizing agents for the isolation of nucleic acids and other compounds, such as biocides for use in agricultural products, or as an absorbent for oils, flavors, fragrances, etc. for use in food, cosmetic, and personal care products. Alternating methods, such as freeze drying, selective co-precipitation, etc., can also be used to produce such products. The methods of manufacturing controlled release formulations containing cellulose beads and cellulose bead immobilizing agents are well known in the art.

Thus, the cellulose excipient of this invention allows for the formulation of a wide variety of pharmaceutical, food, cosmetic, personal care, and agricultural products.

The following examples are offered to illustrate but not limit the invention. Thus, they are presented with the understanding that various formulation modifications as well as method of delivery modifications may be made and still be within the spirit of the invention.

EXAMPLE 1

Preparation of Microfibrillated/Powdered Cellulose (Method A and Method B)

A. To 50 grams of powdered cellulose, about 300 ml of 5N sodium hydroxide solution was slowly added by constant agitation. The resulting paste-like mass was allowed to stand for 12 hours at room temperature and then about 210 ml of ethanol was added with vigorous agitation. This resulted in an immediate precipitation of a fine powder, which was filtered and washed with water until the pH of the filtrate was near neutral. The wet cake was dried in an oven at 50–55° C. and then sieved to different particle size fractions.

B. 50 grams of cotton linter sheet, broken into small pieces, was soaked in about 300 ml of 7.5N sodium hydroxide solution for 24–48 hours. The resulting swollen cotton liter pieces were then washed with water to a neutral pH. The wet cotton linter pieces were suspended in 1N HCl solution, equivalent to a 1:10 w/v ratio, allowed to stand for an hour and then heated at boiling temperature for 2 hours. The resulting solid was filtered, washed with water to a near neutral pH and then dried in air or oven at 50–55° C. The powder fractions having a particle size of between 45–104 $\mu$m and 75–104 $\mu$m were collected and characterized, and the results are shown in Table 1.

TABLE 1

Physical Properties of Microfibrillated/Powdered Cellulose

| | Microfibrillated/Powdered Cellulose | | |
|---|---|---|---|
| | Method A | | Method B |
| Properties | Batch 1 | Batch 2 | Batch 1 |
| Particle size, $\mu$m | 45–104 | 75–104 | 75–104 |
| True density, g/cc | — | 1.544 | — |
| Bulk density, g/cc | 0.469 | 0.401 | — |
| Tap density, g/cc | 0.509 | 0.430 | — |
| Moisture content | NMT 5% | NMT 8% | NMT 8% |

EXAMPLE 2

Tabletting Properties of Microfibrillated/Powdered Cellulose 250 mg of microfibrillated/powdered cellulose, prepared according to the method described in Example 1, was compressed directly on a Carver press at different compression force using a 10-mm diameter set of a die and punches and a dwell time of 10 seconds. All tablets appeared without any defects.

All tablets when placed in water disintegrated in less than 30 seconds. The hardness of tablets prepared at different compression pressures is presented in Table 2.

TABLE 2

Relationship Between Compression Force and Hardness of Microfibrillated/Powdered Cellulose Tablets

| Compression Force (lbs)[a] | Hardness[b] (kp) |
|---|---|
| 500 | 11.8 |
|  | (12.1, 11.4) |
| 1000 | 14.7 |
|  | (15.5, 13.8) |
| 2000 | 19.5 |
|  | (19.3, 19.6) |
| 5000 | 25.9 |
|  | (26.8, 25.0) |

[a]Force read on the Carver Press;
[b]n = 2.

EXAMPLE 3

Preparation of Acetaminophen/Aspirin Tablets 320 mg of acetaminophen or aspirin (USP Powder, CAS-50-78-2), 175 mg of microfibrillated/powdered cellulose or microcrystalline cellulose (Avicel PH-102), and 5 mg of magnesium stearate were homogenously mixed and then compressed on a Carver Press using a 10-mm die and punches and a pressure of 4000 lbs and a dwell time of 1 min. The hardness and disintegration times of tablets are presented in Table 3.

TABLE 3

Evaluation of Acetaminophen/Aspirin Tablets

| Properties | Microfibrillated/Powdered Cellulose | Avicel PH-102 |
|---|---|---|
| Acetaminophen |  |  |
| Hardness (kp) | 2.5 | 4.5 |
| Disintegration time (sec.) | <30 | >60* |
| Aspirin |  |  |
| Hardness (kp) | 6.9 | 9.2 |
| Disintegration time (sec.) | <30 | >60* |

*Splits into halves after 15 sec. Did not disintegrate into powder at all.

EXAMPLE 4

Preferred Method of Preparing Microfibrillated/Powdered Cellulose from Cellulose Pulp or Cotton Linter Sheets The following flow chart illustrates a preferred method of preparing microfibrillated/powdered cellulose.

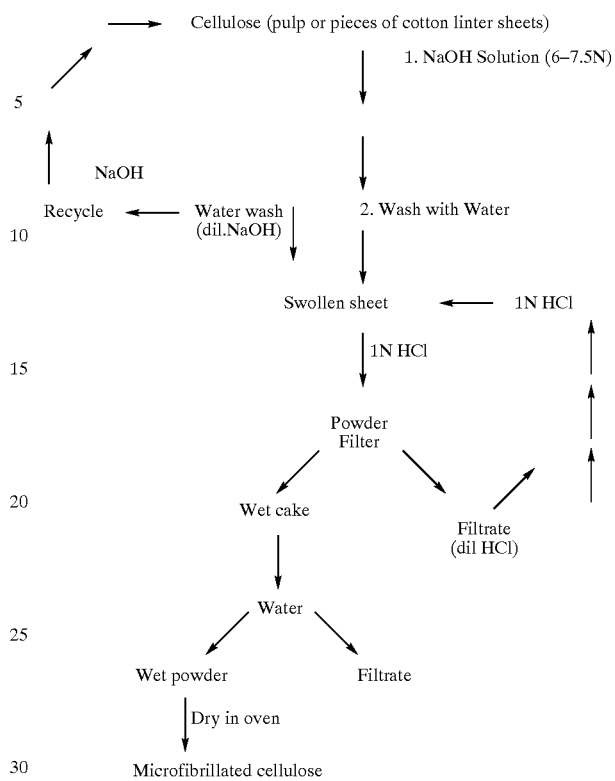

EXAMPLE 5

Preparation of an Aqueous Dispersion of Microfibrillated/Powdered Cellulose

One hundred grams of cotton linter and 600 ml of 7.5N NaOH were reacted according to the procedure described in Example 1B. The swollen cellulose was then treated with 1000 ml 1.0N HCl for 1 hour at room temperature and then at boiling temperature for 1.5 hours. The fine white powder formed was filtered, and washed with water until the filtrate showed a pH of 7 and a negative test for chloride ions. The resulting acid-free wet cake of microfibrillated/powdered cellulose, weighing about 238 g (corresponding to about 85 g of cellulose solid), was placed in 1450 ml of water and homogenized using a laboratory blender or a high shear mixer for 15 minutes or until a stable, milky-looking homogeneous dispersion was formed. The dispersion showed no separation for over two weeks. It was stored in a cold room until use.

EXAMPLE 6

Preparation of Microfibrillated/Powdered Cellulose Beads 250 ml of the aqueous dispersion prepared as described in Example 5 was mixed with 250 ml of water and homogenized for 5 minutes using a blender. The resulting diluted dispersion, corresponding to a solid content of about 2.5%, was spray dried using a laboratory Yamoto G-32 spray dryer, equipped with a standard 2-fluid pressure nozzle with an orifice of 406 □m. The operating conditions were: inlet temperature 190° C.; atomization air pressure 0.5–1 kg.f/cm², drying air flow rate 0.3 ml/min.; outlet temperature 80° C. The feed suspension was constantly stirred during the spray drying processes.

EXAMPLE 7

Preparation of a Co-Spray Dried Microfibrillated/powdered Cellulose and Carboxymethyl Cellulose Product 250 ml of the aqueous dispersion prepared as described in Example 6 and 250 ml of water containing 1.25 g. sodium carboxymethylcellulose were mixed using a blender. The resulting homogeneous dispersion was spray dried using a laboratory Yamoto G-32 spray dryer, equipped with a standard 2-fluid pressure nozzle with an orifice of 406 □m. The operating conditions were as given in Example 6.

EXAMPLE 8

General Method for the Preparation of a Microfibrillated/Powder Cellulose Based Topical Drug Carrier System To an appropriate amount of the aqueous microfibrillated/powdered cellulose dispersion, (equivalent to contain 2.5–10% powdered cellulose solid content), prepared according to the procedure described in Example 6, 0.05–10% of a viscosity enhancing agent selected from a group consisting of water soluble polymers, such as cellulose ethers (e.g., hydroxyethylcellulose, hydroxypropylcellulose, hydroxypropylmethylcellulose, carboxymethylcellulose), polyacrylic acid (e.g., Carbomer), and polyvinyl pyrrolidone, or a highly hydrating but water insoluble inorganic material, such as amorphous silica (e.g., cab-o-sil), magnesium aluminum silicate (Magnabrite™), and Bentonite (e.g., Polargel), and 1–15% of a water miscible/soluble plasticizer (e.g., glycerin, polyethylene glycol, propylene glycol, etc.) were mixed in the order written, using a laboratory mixer or a high shear mixer to produce an adequately plasticized aqueous drug carrier system. To prepare a topical cream or lotion product, appropriate amounts of this dispersion and the drug, in a finely divided powdered form or as a solution in a water miscible solvent such as alcohol, glycerin, or propylene glycol, are mixed using a high shear mixer. If Carbomer (or Carbopol) is used as a viscosity-enhancing agent, the addition of triethanolamine or an aqueous solution of an alkali metal hydroxide is required to achieve the desired viscosity and/or pH of the final product. This general method is applicable for the preparation of topical cosmetic and personal care products. Adequately plasticized topical formulations rub in smoothly on the skin and produce transparent, non-oily, and non-tacky films.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A fibrous cellulose excipient comprising a cellulose II lattice with a bulk density of between 0.2–0.5 g/cm³; and a tap density of between 0.4.–0.7 g/cm³, said excipient not comprising cellulose I.

2. A cellulose excipient according to claim 1 which has X-ray diffraction patterns at 12, 20, and 22° 2θ.

3. A cellulose excipient according to claim 1 which is a partially aggregated fibrous material.

4. A cellulose excipient according to claim 1 that is dried.

5. A cellulose excipient according to claim 1 that is in an aqueous dispersion.

6. A cellulose excipient according to claim 1 that is present in a product selected from the group consisting of a food, a pharmaceutical, an agricultural, a cosmetic, and a cellulose bead composition.

7. A cellulose excipient according to claim 1 which is compressed.

8. A cellulose excipient according to claim 7 that is in a tablet compressed at a force ranging from 500–5000 pounds and having a resulting hardness ranging from 11.8–25.9 kp, said tablet disintegrating in water in less than 30 seconds.

* * * * *